US00PP27790P3

(12) United States Plant Patent
Zaiger et al.

(10) Patent No.: US PP27,790 P3
(45) Date of Patent: Mar. 21, 2017

(54) PEACH TREE NAMED 'SNOW FOX'

(50) Latin Name: *Prunus persica*
Varietal Denomination: Snow Fox

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 134 days.

(21) Appl. No.: 14/544,568

(22) Filed: Jan. 23, 2015

(65) Prior Publication Data

US 2016/0219772 P1 Jul. 28, 2016

(51) Int. Cl.
*A01H 5/08* (2006.01)

(52) U.S. Cl.
USPC ..... Plt./195

(58) Field of Classification Search
USPC ..... Plt./195
See application file for complete search history.

(56) References Cited

U.S. PATENT DOCUMENTS

2013/0263341 P1 * 10/2013 Zaiger ..... A01H 5/0868 Plt./195

* cited by examiner

*Primary Examiner* — June Hwu

(57) ABSTRACT

A new and distinct variety of peach tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having vigorous, upright growth habit.
2. Tree being a regular and productive bearer of large size fruit.
3. Fruit having firm, white flesh with a very good flavor and eating quality.
4. Fruit having an attractive red skin color.
5. Fruit with good storage and shipping qualities.

1 Drawing Sheet

Botanical designation: *Prunus persica.*
Variety denomination: 'Snow Fox'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

Prior Varieties

Among the existing varieties of peach trees, which are known to us, and mentioned herein, 'Sitka' Peach (U.S. Plant Pat. No. 23,799) and our proprietary non-patented peach varieties with the field identification numbers '196LT639', '35M358', '99LH139', '59Z480', '56Z782' and '58ZA508'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. as a first generation cross between our proprietary non-patented peach seedling selections with the field identification numbers '196LT639' and '35M358'. The proprietary non-patented peach seed parent (196LT639) originated from a cross between the proprietary non-patented peach seedling selections '99LH139' and '59Z480'. The proprietary non-patented peach pollen parent (35M358) originated from a cross between the proprietary peach seedling selections '56Z782' and '58ZA508'. A large number of these first generation seedlings were budded onto older established trees of 'Nemaguard' Rootstock (non-patented) to enhance earlier fruit production. Under close and careful observation we recognized the desirable tree and fruit characteristics of the present seedling and selected it in 2007 for additional asexual propagation and commercialization.

ASEXUAL REPRODUCTION OF THE VARIETY

In 2007 asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of peach tree (*Prunus persica*) is of large size, vigorous, upright growth and a regular and productive bearer of large size, clingstone fruit.

The fruit is further characterized by its firm, white flesh, having an attractive red skin color with very good flavor and eating quality. In comparison to its non-patented peach seed parent '196LT639' the fruit of the new variety is larger in size and is 21 days later in maturity. In comparison to its non-patented peach pollen parent '35M358' the fruit of the new variety is larger in size, has white flesh compared to yellow and has a lower winter chilling requirement. In comparison to the commercial variety 'Sitka' Peach (U.S. Plant Pat. No. 23,799) the fruit of the new variety has superior flavor and is larger in size. In comparison to 'Snow Baby' (US 2013/0263341 P1), which is the sister sibling of the present variety, with both being grown together on original mother tree on separate scaffolds and having the exact same cultural conditions, we found these differences; the fruit of the new variety being 4 days earlier in maturity, being larger in size, having a lighter red skin color, and its flowers blooming 2 days earlier. Having a lower chilling requirement of approximately 50 hours allows the new variety to be planted in more southern growing areas that have fewer chilling hours. 'Snow Baby' (US 2013/0263341 P1) has a higher chilling requirement that allows it to be grown in more northern areas that would be unsuitable for the new variety. The new variety has fewer areas of exposed ground color on the skin and does not have the speckled appearance that 'Snow Baby' (US 2013/0263341 P1) exhibits.

DESCRIPTION OF THE PHOTOGRAPH

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 7 year old specimens grown near Modesto, Calif., with color in accordance with Munsell Book of Color published in 1958.

Tree:

*Size*.—Large, usually pruned to 3 to 3.5 meters in height and width for economical harvesting of fruit. Varies with different cultural practices.

*Vigor*.—Vigorous, tree growth of approximately 1.5 to 2 meters in height the first growing season. Varies with cultural practices, soil type, fertility and climatic conditions.

*Form*.—Upright growth, usually pruned to vase shape.

*Branching habit*.—Upright, crotch angle approximately 35°, increases with heavy crop load.

*Productivity*.—Productive, thinning and spacing of fruit desirable for marketable size. Fruit set varies with climatic conditions during bloom time.

*Bearer*.—Regular, has had adequate fruit set 5 consecutive years. No alternate bearing observed.

*Fertility*.—Self fertile.

*Density*.—Medium dense, usually pruned to vase shape to increase amount of sunlight to center of tree to enhance fruit color, Brix and health of fruit wood.

*Hardiness*.—Hardy in all stone fruit growing areas of California. Tree grown in USDA Hardiness Zone 9. Winter chilling requirement approximately 550 hours at or below 45° F.

Trunk:

*Size*.—Large. Average circumference 45.7 cm at 22.9 cm above ground on a 7 year old tree.

*Stocky*.—Medium stocky.

*Texture*.—Medium shaggy, roughness increases with age.

*Color*.—Varies from 7.5Y 4/2 to 5Y 4/2.

Branches:

*Size*.—Medium. Average circumference 12.7 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 27 in a 25.8 square cm section. Average length 2.7 mm. Average width 1.6 mm. Color varies from 7.5YR 5/10 to 7.5YR 6/10.

*Color*.—New growth varies from 2.5GY 6/6 to 2.5GY 6/8. Mature growth varies from 7.5YR 3/4 to 10YR 3/4, varies with age of growth.

Leaves:

*Size*.—Medium to large. Average length 138.6 mm. Average width 43.9 mm.

*Form*.—Elliptical.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surface glabrous.

*Petiole*.—Medium. Average length 10.7 mm. Average width 1.6 mm. Longitudinally grooved. Surface — glabrous. Color varies from 5GY 5/8 to 5GY 4/8.

*Glands*.—Type — reniform. Size — medium to large. Average length 1.3 mm. Average diameter 0.9 mm. Average number 3, varies from 2 to 4. Located primarily on the base of the leaf blade and upper portion of the petiole. Color varies from 5GY 6/8 to 5GY 5/8.

*Stipules*.—Average number 2. Average length 10.1 mm. Edges — pectinate. Color varies from 5GY 6/8 to 5GY 5/8.

*Color*.—Upper surface varies from 5GY 3/6 to 5GY 3/4. Lower surface varies from 5GY 4/4 to 5GY 5/4. Midvein color varies from 10Y 6/6 to 10Y 7/6.

Flower buds:

*Size*.—Large. Average length 19.1 mm. Average diameter 9.8 mm.

*Hardiness*.—Hardy with respect to California winters.

*Density*.—Medium.

*Form*.—Conical, becoming elongated just before opening.

*Pedicel*.—Average length 4.5 mm. Average width 1.4 mm. Color varies from 2.5GY 6/4 to 2.5GY 5/6. Surface glabrous.

*Color*.—Varies from 5RP 7/8 to 7.5RP 7/8.

Flowers:

*Blooming period*.—Date of First Bloom Feb. 5, 2014. Date of Petal Fall Feb. 15, 2014, varies slightly with climatic conditions.

*Size*.—Large, showy. Average height 21.8 mm. Average diameter 36.7 mm.

*Petals*.—Normally 5, alternately arranged to sepals. Size — large. Average length 16.8 mm. Average width 16.6 mm. Form — orbicular. Arrangement — overlapping. Petal apex — rounded. Petal base — rounded to somewhat truncated. Margin — sinuate. Color varies from 5RP 9/2 to 5RP 8/4, fades with age of flower. Both upper and lower surface — glabrous.

*Sepals*.—Normally 5, alternately arranged to petals. Size — large. Average length 5.5 mm. Average width 5.5 mm. Shape — ovate. Sepal apex — rounded. Margin — entire. Surface — upper surface glabrous, lower surface pubescent. Color — upper surface varies from 5GY 5/6 to 7.5R 3/6. Lower surface varies from 5R 2/4 to 7.5R 2/4.

*Stamens*.—Average number per flower 49. Average filament length 15.7 mm. Filament color varies from N 9.5/(white) to 5RP 6/8 depending, on age of flower. Anther color varies from 7.5R 3/10 to 7.5R 3/12. On average, the stamens are above the height of the petals.

*Pollen*.—Self fertile. Color varies from 2.5Y 7/10 to 2.5Y 7/12.

*Pistil*.—Normally 1. Average length 16.3 mm. Position of stigma an average of 2.1 mm below anthers. Surface — pubescent. Ovary — pubescent. Color varies from 10Y 7/6 to 2.5GY 7/6.

*Fragrance*.—Slight.

*Color*.—Varies from 5RP 8/4 to 5RP 7/6.

*Pedicel*.—Average length 4.1 mm. Average width 1.3 mm. Color varies from 2.5GY 5/6 to 5GY 5/6. Surface glabrous.

*Number flowers per flower bud*.—Normally one.

Fruit:

*Maturity when described*.—Firm ripe and ready for consumption.

*Date of first picking*.—May 30, 2014.

*Date of last picking*.—Jun. 9, 2014, varies slightly with climatic conditions.

*Size*.—Large. Average diameter axially 71.3 mm. Average transversely in suture plane 75.8 mm. Average weight 249.9 grams, varies slightly with fertility of the soil, amount of thinning and climatic conditions.

*Form*.—Globose.

*Suture*.—Nearly smooth, extends from base to apex.

*Ventral surface*.—Nearly smooth.

*Apex*.—Slightly retuse.

*Base*.—Retuse.

*Stem cavity*.—Rounded to slightly elongated in suture plane. Average depth 13.7 mm. Average diameter 9.4 mm.

Stem:

*Size*.—Small to medium. Average length 9.5 mm. Average diameter 3.3 mm.

*Color*.—Varies from 2.5GY 6/8 to 2.5GY 6/10.

Flesh:

*Ripens*.—Evenly.

*Texture*.—Firm, meaty.

*Fibers*.—Few, small, tender.

*Firmness*.—Firm, comparable to other commercial varieties.

*Aroma*.—Moderate.

*Amydgalin*.—Undetected.

*Eating quality*.—Very good.

*Flavor*.—Very good, good balance between acid and sugar.

*Juice*.—Moderate amount, enhances flavor.

*Acidity*.—Not available.

*Brix*.—Average Brix 11.0°, varies slightly with amount of fruit per tree and climatic conditions.

*Color*.—Varies from 7.5Y 9/12 to 10Y 9/2. The anthocyanin coloration next to the skin and the slight bleeding into the flesh near the stone varies from 2.5R 6/6 to 2.5R 5/8.

*Pit cavity*.—Average length 35.9 mm. Average width 25.2 mm. Average depth 11.1 mm. Color varies from 7.5Y 8.5/4 to 10Y 8.5/4.

Skin:

*Thickness*.—Medium.

*Surface*.—Smooth.

*Pubescence*.—Moderate amount, very short.

*Tendency to crack*.—None.

*Color*.—Ground color varies from 7.5Y 9/2 to 7.5Y 8.5/4. Overspread with 7.5R 2/8 to 7.5R 3/10.

*Tenacity*.—Tenacious to flesh.

*Astringency*.—Undetected.

Stone:

*Type*.—Clingstone, strong adherence to flesh.

*Size*.—Large. Average length 34.9 mm. Average width 24.2 mm. Average thickness 20.2 mm.

*Form*.—Ovoid.

*Base*.—Flat.

*Apex*.—Slightly pointed. Average length 1.4 mm.

*Surface*.—Pitted throughout, pits vary from rounded to slightly elongated.

*Sides*.—Unequal, one side extending further from the suture plane.

*Ridges*.—Relatively smooth, narrow ridges extending from base toward apex.

*Tendency to split*.—None.

*Color*.—Varies from 7.5YR 6/6 to 7.5YR 4/8 when dry. Anthocyanin coloration varies from 2.5R 5/8 to 5R 5/8 when first exposed from the flesh.

Kernel:

*Size*.—Large. Average length 18.7 mm. Average width 10.8 mm. Average depth 6.0 mm.

*Form*.—Ovoid.

*Viability*.—Partially viable, some embryos with incomplete development.

*Skin color*.—Varies from 7.5Y 9/4 to 10Y 9/2.

Use:

*Dessert*.—Market — local and long distance.

Keeping quality: Good, held firm in cold storage for 3 weeks at 38° to 42° F. without shriveling, internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices. The present new variety of peach tree, its flowers foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

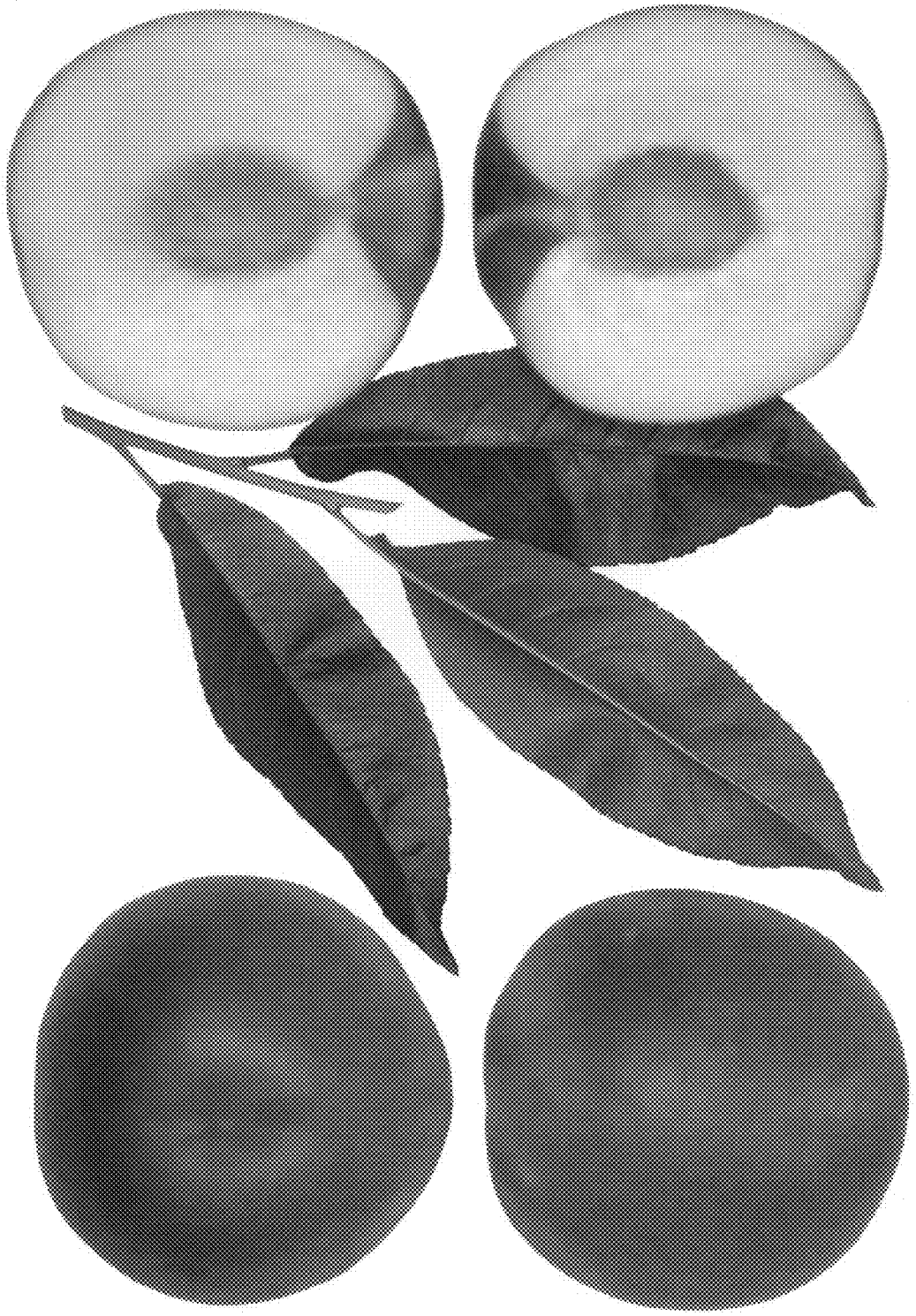

* * * * *